(12) United States Patent
Nieuwenhuis et al.

(10) Patent No.: US 9,254,488 B2
(45) Date of Patent: Feb. 9, 2016

(54) AUTOMATED SYSTEM FOR SELECTIVELY PROCESSING A SAMPLE

(75) Inventors: Jeroen Nieuwenhuis, Eindhoven (NL); Toon Evers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 449 days.

(21) Appl. No.: 13/808,820

(22) PCT Filed: Jun. 24, 2011

(86) PCT No.: PCT/IB2011/052773
§ 371 (c)(1),
(2), (4) Date: Jan. 7, 2013

(87) PCT Pub. No.: WO2012/004704
PCT Pub. Date: Jan. 12, 2012

(65) Prior Publication Data
US 2013/0112018 A1    May 9, 2013

(30) Foreign Application Priority Data

Jul. 9, 2010    (EP) .................................... 10169034

(51) Int. Cl.
*G01N 37/00* (2006.01)
*B01L 3/00* (2006.01)
G01N 21/552 (2014.01)
G01N 35/00 (2006.01)
G01N 35/04 (2006.01)

(52) U.S. Cl.
CPC .......... *B01L 3/505* (2013.01); *G01N 35/00029* (2013.01); *G01N 21/552* (2013.01); *G01N 35/00009* (2013.01); *G01N 35/0098* (2013.01); *G01N 2035/00148* (2013.01); *G01N 2035/0436* (2013.01)

(58) Field of Classification Search
CPC .................................... G01N 1/00; G01N 1/28
USPC ......................................................... 73/864.91
See application file for complete search history.

(56) References Cited

U.S. PATENT DOCUMENTS

| | | | |
|---|---|---|---|
| 2003/0044323 A1 | 3/2003 | Diamond et al. | |
| 2004/0009614 A1* | 1/2004 | Ahn et al. | 436/526 |
| 2004/0197233 A1 | 10/2004 | Nagaoka et al. | |
| 2006/0120926 A1 | 6/2006 | Takada et al. | |
| 2007/0148052 A1 | 6/2007 | Hiramatsu et al. | |
| 2009/0065368 A1 | 3/2009 | Davis et al. | |
| 2009/0155123 A1 | 6/2009 | Williams et al. | |

(Continued)

FOREIGN PATENT DOCUMENTS

| | | |
|---|---|---|
| WO | 02090995 A2 | 11/2002 |
| WO | 2004055522 A1 | 7/2004 |
| WO | 2008155716 A1 | 12/2008 |
| WO | 2009094642 A2 | 7/2009 |
| WO | 2010035204 A1 | 4/2010 |

*Primary Examiner* — Hezron E Williams
*Assistant Examiner* — Rodney T Frank

(57) ABSTRACT

A method and system for selectively processing a sample according to one of a plurality of different assays, for example, for detecting a certain target component in the sample, include a plurality of cartridges in which the processing of a sample can take place and which each contain a different set of reagents required for one of the assays. Moreover, the system further includes a manipulator for introducing a sample into a selected one of the cartridges. Depending on the assay to be performed with a sample at hand, the appropriate cartridge is chosen, and the sample is introduced into and processed in the cartridge.

19 Claims, 6 Drawing Sheets

(56) References Cited

U.S. PATENT DOCUMENTS

| | | |
|---|---|---|
| 2010/0028985 A1 | 2/2010 | Hanafusa et al. |
| 2010/0159487 A1 | 6/2010 | Holtlund et al. |
| 2012/0107961 A1* | 5/2012 | Dittmer et al. ............... 436/501 |
| 2013/0109106 A1* | 5/2013 | Klunder et al. ............... 436/180 |

* cited by examiner

AUTOMATED SYSTEM FOR SELECTIVELY PROCESSING A SAMPLE

FIELD OF THE INVENTION

The invention relates to a system and a method for processing a sample according to a selected one of a plurality of assays, particularly for detecting selected target components in a biological sample. Moreover, it relates to a design of a cartridge that can be used in such a system.

BACKGROUND OF THE INVENTION

From the WO 2008/155716 A1 a biosensor is known in which target components labeled with magnetic beads are detected by frustrated total internal reflection (FTIR) at the sensing surface of a cartridge. The described biosensor is particularly designed and suited for point-of-care applications, for example roadside drug tests.

SUMMARY OF THE INVENTION

Based on this background it was an object of the present invention to provide means that allow the processing of a sample in a stationary, high-throughput laboratory environment.

According to a first aspect, the invention relates to a system for processing a sample according to a selected one of a plurality of assays, particularly immunoassays. The sample may typically be a biological fluid, for example saliva or blood. The assays comprise the instructions how a sample at hand shall be processed in order to achieve a desired result, wherein the processing may comprise any arbitrary steps, including the physical and/or chemical modification of the sample. The aim of the assays may for example be the detection of different target components in a sample, for example of proteins, small molecules, antibodies, DNA, or the like. The processing steps of the assays will typically require the use of specific reagents. In view of this, the system comprises the following components:

a) A plurality of cartridges in which the processing of a sample can take place and which each contain a different set of reagents required for one (preferably only one or a few) of the assays. With other words, the reagents of one cartridge are associated to one of the assays and are generally not suitable or needed for the other assays. It should be noted that a "set" of reagents may in the most simple case comprise just one reagent. The term "cartridge" shall denote an exchangeable element or unit that can accommodate a sample. The cartridge will usually be a disposable component which is used only once for a single sample.

b) A manipulator for automatically introducing a given sample into a selected one of the aforementioned cartridges. The manipulator may for instance comprise a robot arm that can transfer components from one location to another.

The described system has the advantage that the cartridges comprise already reagents required for the assay to be performed and simultaneously provide the physical environment for the processing. This facilitates the demands of available space and reduces the handling steps that have to be done. In the preferred case that a cartridge comprises already all the reagents needed for a given assay, the introduction of the sample into the cartridge is the only handling step with materials the manipulator has to do.

While each cartridge may comprise the reagents needed for one and only one assay, it is preferred that at least one cartridge contains the reagents for several assays, preferably for up to four assays. By combining in a single cartridge reagents for assays that are typically requested in combination the price per test can be significantly reduced. It is therefore preferred that all cartridges each comprise reagents for several assays.

It should be noted that the cartridges are usually present in a given system in many identical copies, such that a plurality of the same or of different assays can be performed with the system. In this sense, the term "cartridge" usually represents a whole type, set, or category of components.

According to a second aspect, the invention comprises a method for processing a sample according to a selected one of a plurality of assays, said method comprising the following steps:

a) Provision of a plurality of different cartridges in which the processing of a sample can take place and which each contain a different set of reagents required for one of the assays.

b) Introducing with a manipulator a sample into a selected one of the aforementioned cartridges.

The method comprises in general form the steps that can be executed with a system of the kind described above. Reference is therefore made to the above description for more information about the details, advantages, and modifications of the method.

In the following, various preferred embodiments of the invention will be described that relate to both the system and the method of the kind described above.

Thus it is preferred that the cartridges are designed in such a way that they enable execution of a complete assay with a sample added to the cartridge without further liquid handling steps, i.e. without the addition and/or transfer of liquid materials (besides the sample itself). In particularly, the cartridge may be designed such that a sample added to the cartridge reaches all the associated reagents without further handling steps. The reagents associated to the same assay may for example be disposed in one and the same sample chamber of the cartridge.

Furthermore, it is preferred that the system is accommodated in a housing. The cartridges are then stored inside the instrument, and it is not necessary to (manually) insert a cartridge with each test.

It was already said that the system and the method are suited for a high-throughput environment. Preferably, they are adapted to perform more than 20 tests/hour, preferably more than 50 tests/hour, most preferably more than 150 tests/hour.

The cartridges used in the system or method may preferably have a foil-based design, i.e. they comprise at least one layer made from a flexible sheet (foil). Preferably, all the layers of the cartridge are made from foils.

According to another preferred embodiment, several copies of the cartridges are arranged in the reach of the manipulator. Thus a plurality of samples can automatically be processed in series and/or in parallel.

In another embodiment, a waste reservoir is arranged in the reach of the manipulator. Materials can then readily be disposed of at the end of an assay. As the cartridges are typically disposable units, used cartridges can be discarded in the waste reservoir, too.

At least one of the cartridges comprises dry reagents. Preferably all the reagents of one cartridge and/or of all cartridges are dry reagents. In this case the only liquid involved in an assay is the sample liquid itself; this significantly reduces the volume of (liquid) waste.

The system or the method may further preferably comprise a readout-device in which target components of a sample can be detected, wherein said sample is preferably provided to the readout-device in one of the cartridges. The detection of target components may apply optical, electrical, magnetic, acoustic, radioactive or any other suitable measurement principles. For optical detection, the readout-device may for example comprise a light source for illuminating a sample in a cartridge and a light detector for measuring light emitted from the sample (particularly by an FTIR process).

The system or the method may also preferably comprise at least one actuation-device in which a sample comprised in a cartridge can be actuated, preferably by the action of electromagnetic fields and/or heat. The actuation-device may particularly comprise a magnetic field generator, for example a permanent magnet or an electromagnet. The inclusion of an actuation-device increases considerably the menu of assays that can be executed. The number of possible assays can even more be increased if several different actuation-devices are comprised by the system. Moreover, it is possible to provide several identical copies of an actuation-device so that a plurality of assays can be done in parallel.

In another embodiment of the invention, the system or the method comprises at least one integrated actuation-and-readout device. This reduces the handling steps to be done by the manipulator, because a sample (in a cartridge) can be delivered in one step to both an actuation and detection process.

Of course any combination of the above embodiments can be applied, yielding a general architecture with N readout-devices, M actuation-devices, and L actuation-readout-devices (N, M, L=0, 1, 2, ... ).

Moreover, the at least one of the above mentioned readout-devices, actuation-devices, and/or actuation-and-readout devices may optionally be movable by the manipulator together with a cartridge. This allows to perform some actuation and/or detection even while a cartridge (with a sample) is transported. For example, if the actuation-device comprises a magnet, the exertion of magnetic forces on a sample can favorably be continued during the movement of a cartridge.

The reagents of the cartridges may for example comprise binding sites that are specific for different target components which may be present in a sample. As usual, the term "binding sites" shall denote reagents that are immobilized on a surface (of a cartridge) and that specifically bind to certain (usually labeled) target components, thus immobilizing these, too. Additionally or alternatively, the reagents of the cartridges may comprise label particles that selectively bind to one target component which may be present in a sample. In general, the term "label particle" shall denote a particle (atom, molecule, complex, nanoparticle, microparticle etc.) that has some property (e.g. optical density, magnetic susceptibility, electrical charge, fluorescence, radioactivity, etc.) which can be detected, thus indirectly revealing the presence of the associated target component. Typical examples of label particles are magnetic beads.

The cartridges of the system and/or lots in which cartridges are supplied to the system may optionally be provided with automatically readable information carriers, comprising for example information about calibration parameters. Thus the need for additional calibration steps within the system can be avoided.

At least one cartridge may preferably comprise a plurality of sample chambers in which different assays can be executed. Thus multiple assays can be run in parallel on the same disposable cartridge, reducing the cost per assay results.

The cartridge that is used in the system or the method described above may preferably have a sample chamber in which examinations can be made, particularly optical examinations. For the optical examinations, the whole cartridge or at least a part of the cartridge may be transparent, for example made from transparent plastic. Moreover, the transparent part of the cartridge may be provided with suitable optical elements like prismatic or lens-like protrusions or embossings, gratings, polished surface areas etc. Most preferably, the cartridge is adapted to allow the examination of a sample in the sample chamber by frustrated total internal reflection (FTIR) of light emitted into the cartridge.

According to a third aspect, the invention relates to a cartridge which may be used in the above system or method and in other applications, too. Such a cartridge comprises the following components:

a) A sample chamber that is accessible from its top side for adding a sample, for example by a pipette-tip. In particular, the sample chamber may be (completely) open at its top side.

b) Optical structures for the incoupling and outcoupling of light, wherein a sample in the sample chamber can be examined with said light. The optical structures may for example comprise prismatic or lens-like protrusions or embossings, gratings, polished surface areas etc.

Leaving the top side of the sample chamber accessible simplifies the production of the cartridge as no components like fluidic structures are needed and as chemicals like binding sites can more readily be applied to the (bottom) surface of the sample chamber. Moreover, the cartridge is more readily accessible for filling it with a sample and/or with reagents, and the filling is achieved quasi instantaneously (instead of slowly as if the fluid has to move along channels).

To protect the described cartridge against a possible contamination, particularly during times while it is on stock or transported, it is preferred that a lid is provided for closing the top side of the sample chamber, wherein the lid is designed such that it does not hamper the free accessibility of the sample chamber through the top side. To this end, the lid may for example be removable or readily destructible if access is required. The lid may optionally be attached to the cartridge, for example via a hinge, or it may be a separate (removable) component. A removable lid may optionally be reused many times (particularly if has some elaborate design), even if the associated cartridges are discarded. For this reason, the scope of the present application also extends to the lid as an article of its own, independent of the cartridge it shall be used with.

The aforementioned lid can be realized in the various ways. According to a first embodiment, the lid may for example comprise a magnet. A magnet is typically needed in assays using magnetic particles. Combining the functions of a lid and a magnet has the advantage that only one part is needed and that the magnet can come into close proximity to a sample in the sample chamber. Preferably, such a lid with a magnet constitutes a component that is reused as often as possible.

According to another embodiment, the lid comprises a slanted interior surface and an air vent, wherein said air vent is disposed at the highest position of the lid. When such a lid is placed on a cartridge in which the sample chamber is already filled with a liquid, no gases are trapped as they can leave the sample chamber through the air vent.

In another embodiment, the lid is realized by a pierceable foil. The foil may for instance be applied to the sample chamber during the production of the cartridge. Piercing of the foil can for example be readily done with a pipette.

In all the above embodiments of a lid, (dry) reagents may optionally be attached to said lid. If the lid is separate from the cartridge, selection and addition of reagents can hence be achieved by adding the appropriate lid (with reagents) to a cartridge.

The invention further relates to the use of a system or cartridge of the kind described above for molecular diagnostics, biological sample analysis, chemical sample analysis, food analysis, and/or forensic analysis, particularly in a high-throughput automated laboratory environment. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiment(s) described hereinafter. These embodiments will be described by way of example with the help of the accompanying drawings in which.

Like reference numbers or numbers differing by integer multiples of 100 refer in the Figures to identical or similar components.

DESCRIPTION OF PREFERRED
EMBODIMENTS

Figure 1:
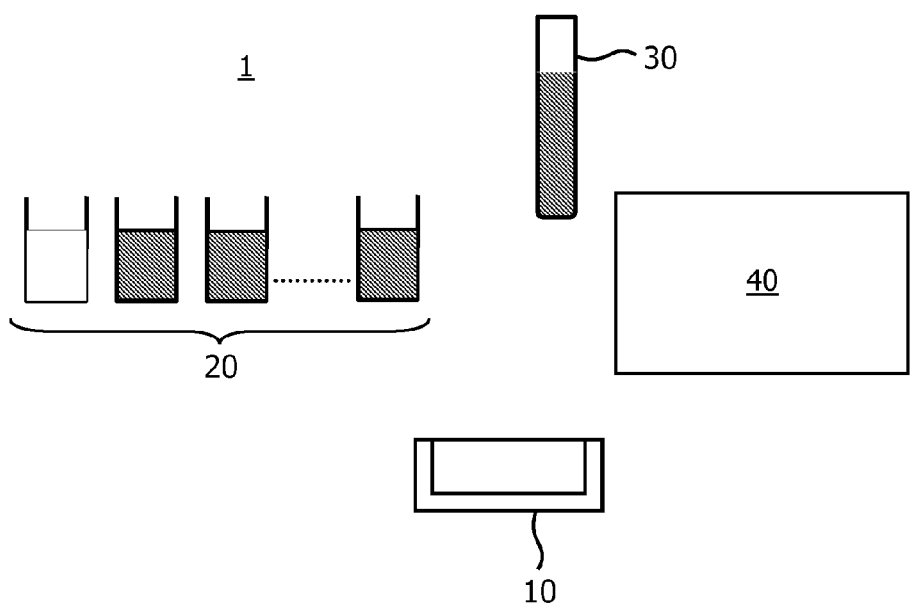
FIG. 1 schematically illustrates an automated system for the examination of samples according to the state of the art.

Biosensors based on nanoparticle labels, particularly nanoparticles that can be actuated with electromagnetic fields ("magnetic beads"), are for example know from the WO 2008/155716 A1. Typically, the magnetic beads are functionalized with antibodies that can bind a specific target molecule. The beads are attracted to the sensor surface, where the number of bound beads is directly or inversely related to the amount of target molecules present in the sample. The beads can then be detected using any technique that is more sensitive to beads that are close to the surface, e.g. frustrated total internal reflection (FTIR). Using this technique, the sensitivity to the nanoparticle labels decreases exponentially with an increasing distance from the surface. The described technology has been developed for point-of-care (POC) applications. In contrast to this, the majority of immunoassay testing is carried out in central laboratories, where large instruments are used. FIG. 1 schematically illustrates such a laboratory system 1 for the execution of different assays with a sample 30 (typically plasma or serum). The system is based on the so-called random access concept and comprises a manipulator 40, which is controlled by a computer with appropriate software (not shown). The manipulator 40 can take a sample to be investigated and transfer it to an open reaction vessel 10. Moreover, the robot has access to a supply 20 of different wet reagents. Depending on the assay to be performed, the robot can take the required reagents one by one from this supply 20 and add them to the reaction vessel 10. By various pipetting and incubation steps the complete assay is carried out. Finally the reaction vessel 10 is transferred to a detection-device (not shown) to quantify the outcome of the assay.

The essence of such a system 1 is that a number of robotized sample and reagent handling steps of an assay is executed in an empty reaction vessel 10 that can be used for any test, where the specific reagents that determine the type of test are added later.

Although the described robotized system concept is quite flexible and can handle many samples per hour, there are some drawbacks:

The use of robotics is an expensive solution, resulting high instrument cost.

To accommodate all the robotized handling, the instruments are quite large, occupying expensive floor-space in the laboratory.

The volumes of (wet) reagents used are typically quite high resulting in high waste disposal costs (both the servicing aspect of the instrument as well as the actual disposal of the biological waste). Moreover, also other waste is generated, e.g. the pipette tips used.

It is therefore desirable to provide a system that allows a simplified yet accurate execution of a plurality of different assays with a sample.

A solution for this problem is based on the use of pre-loaded cartridges that already contain the reagents required for a specific test. When all reagents required to run an assay are contained in the disposable cartridge, many of the robotized sampling steps can be removed, thus significantly reducing the cost of the instrument. The only liquid handling step required would be to transfer the sample onto the disposable cartridge, minimizing the amount of robotics required.

The use of pre-loaded disposable cartridges that already contain the right amount of reagents enables using dry reagents (instead of wet reagents). When dry reagents are used the only liquid involved in an assay is the sample liquid itself; this significantly reduces the volume of (liquid) waste. Additional advantages of the use of dry reagents include:

Sensitivity: the analyte concentration is no longer diluted by adding the wet reagents.

Stability of the reagents: reagents in a dry form are typically more stable than wet reagents enabling better shelf life.

Storage: Wet reagents typically have to be stored refrigerated, whereas (cartridges with) dry reagents can be stored at room temperature, thus reducing complexity and cost of the instrument.

Figure 2:
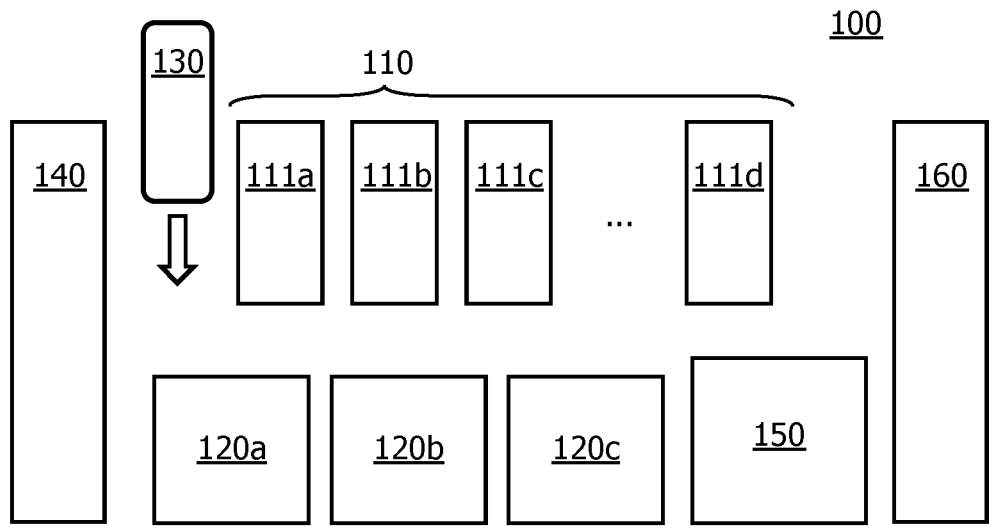
FIG. 2 schematically illustrates an automated system for the examination of samples using pre-filled cartridges and separate actuation and detection-devices according to a first embodiment of the invention.

FIG. 2 illustrates a first particular embodiment of the above solution. This embodiment comprises an instrument or system 100 for selectively performing one of a plurality of different possible assays. The system is characterized in that it comprises a supply 110 with a plurality of (disposable) cartridges 111a, . . . 111d. The cartridges 111a, . . . can be identical or similar in design to cartridges known from for example the WO 2008/155716 A1. Each of these cartridges comprises all the reagents (label particles and binding sites)

that are needed to perform a certain assay, i.e. to detect a particular target component in a sample 130. In a preferred embodiment, the assay principle could be based on the use of magnetic particles as labels since the use of magnetic labels enables a good stringency without the need for any liquid washing steps. The system 100 may be able to work with plasma, serum, whole blood (which may require removal of blood cells). The system concept is not limited to immunoassay but can also be extended to clinical chemistry applications and to other assay types as well.

The disposable cartridges can be stored in the system 100 in various forms:

As shown in FIG. 2, individual cartridges 111a, . . . 111d may be stored as a supply 110 from which a single cartridge is taken every time a test is executed.

The individual cartridges may also be placed on a reel (not shown) that can be pulled through the instrument, or the cartridge may be picked from the reel.

The cartridges may be all linked together on a larger foil (e.g. roll or sheet), which can be moved through the system or of which a single cartridge can be cut.

Figure 4:
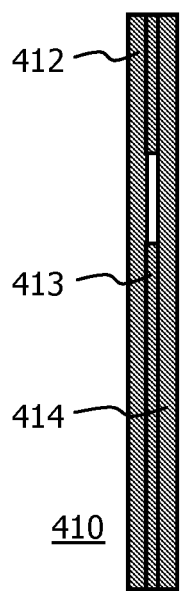
FIG. 4 schematically shows a sectional side view of a cartridge for dipping.
Figure 5:
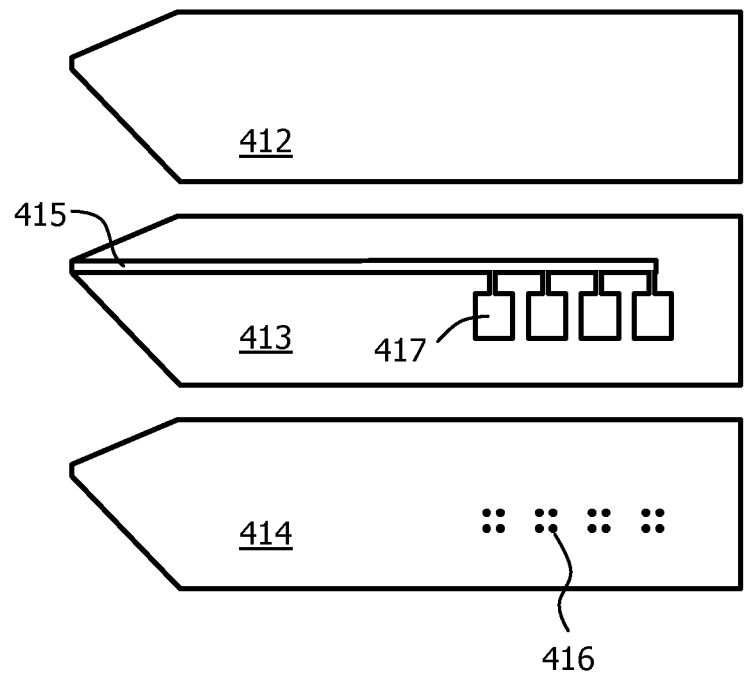
FIG. 5 schematically shows the three foil-layers of the cartridge of FIG. 4.

After a disposable cartridge has been selected, the sample 130 has to be transferred to it. In principle there are two different ways to achieve this:

By transferring the cartridge to the sample and contacting the sample to transfer some of the sample, e.g. by using a cartridge that has a capillary pick-up (cf. FIGS. 4 and 5).

Figure 6:
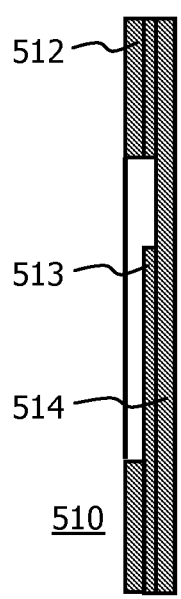
FIG. 6 schematically shows a sectional side view of a cartridge for sample deposition.
Figure 7:
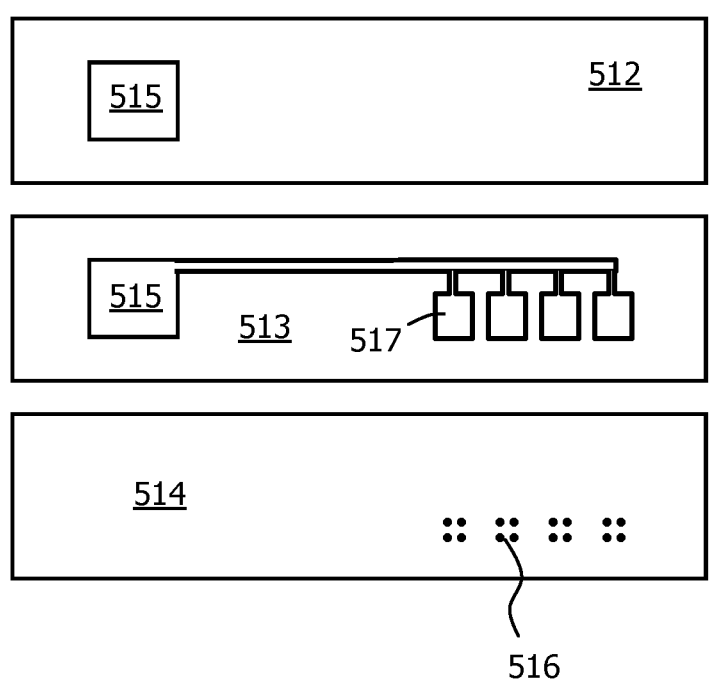
FIG. 7 schematically shows the three foil-layers of the cartridge of FIG. 6.
Figure 8:
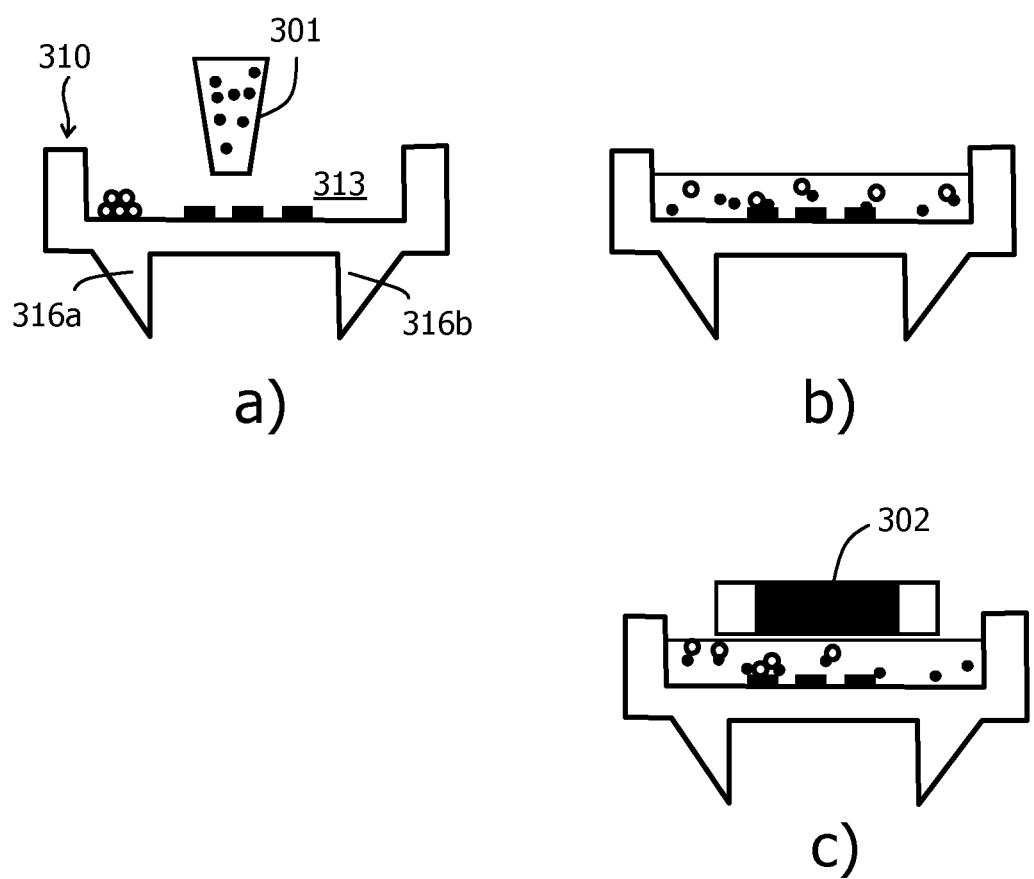
FIG. 8 schematically shows the filling of a cartridge with an open top side.

By a single sample transfer step in which a volume of sample is picked up and is transferred to the cartridge, e.g. by a single pipetting step (cf. FIGS. 6 and 7).

Once the sample is added to the cartridge, the reagents dissolve and react with the sample liquid. Typically some incubation period is required for the reagents to react. In a preferred embodiment a homogeneous assay format is used, reducing the required complexity of the cartridge. Certain assays may require a two-step format, which can be accommodated by using some microfluidic features in the cartridge.

Many assay principles may require some form of external actuation to the disposable cartridge, e.g. heating or the use of external magnetic forces. After sample application, the cartridge may therefore optionally be loaded into an actuation unit 120a, . . . 120c of the instrument that enables certain forms of external actuation.

After the assay has been executed, the outcome of the assay should be detected. Different principles may be used which include, but are not limited to: optical, electrical, magnetic, acoustical detection. The detection may particularly be based on frustrated total internal reflection (FTIR), which is described in the WO 2008/155716 A1. For the detection of the target components of interest, the cartridge with the sample is transferred by the manipulator 140 to a detection unit 150.

After the result has been detected, the disposable cartridge may be transferred to a waste reservoir 160. Since the liquid waste is contained in the cartridge, deposition of the disposable can be very straightforward.

The system 100 comprises multiple (different or identical) actuation-devices 120a, . . . 120c that can handle multiple disposable cartridges at the same time to increase throughput. Similarly, the system could comprise a plurality of detection units (not shown). In the system 100 of FIG. 2, the actuation-devices 120a, . . . 120c and the detection-device 150 are separate, which is favorable since the read-out position typically requires the most expensive components and is used during a relatively short period of the entire assay.

Figure 3:
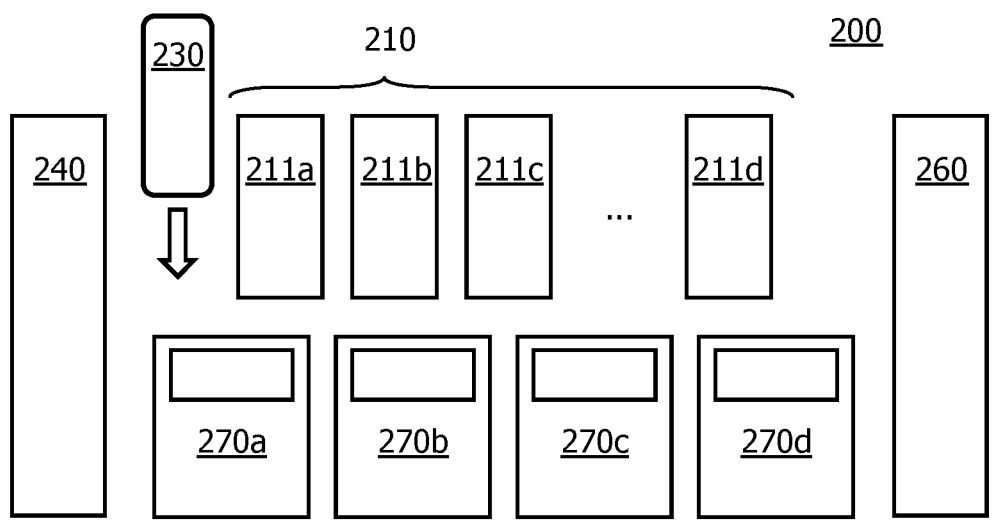
FIG. 3 schematically illustrates an automated system for the examination of samples using pre-filled cartridges and combined actuation-and-readout devices according to a second embodiment of the invention.

FIG. 3 shows an alternative second embodiment of a system 200 with a plurality of cartridges 211a, . . . 211d in a supply 210 and a robot 240 for handling of the sample 230 and cartridge transferring to a waste reservoir 260. In this system 200, the actuation and the detection are combined in a single position, i.e. in actuation-and-readout devices 270a, . . . 270d to save space.

It should be noted that the actuation-devices (e.g. the magnets) may optionally also be transported together with every disposable cartridge, while the detection-devices are fixed at a single or multiple positions. As the performance and reproducibility of an assay with magnetic beads is highly related to the magnet positions, this has the advantages that the control over the assay is uncompromised and many assays can be run simultaneously while the number of expensive readout units is limited.

The described systems are optimally suited as a high-throughput centralized laboratory architecture, in which typically a rate of about 200 assays performed per hour is achieved. When the typical time to run an assay is about 5-10 minutes and typically two to four assays are combined on a single cartridge in the above system, there would be a need for about five to ten actuation positions. For a typical menu of 50 different supported assays on the instrument and with two to four assays on a single disposable cartridge, about 12 to 25 different types of cartridges need to stored in the system.

FIG. 4 shows in a sectional side view a foil-based disposable cartridge 410 for dipping. FIG. 5 shows a top view onto the three separate layers (foils) that constitute this cartridge, i.e. a cover layer 412, a middle layer 413 comprising cavities for an inlet-channel 415 and sample chambers 417, and a bottom layer 414 with spots 416 of binding sites. Due to the several sample chambers, multiple assays can be run in parallel on the same disposable cartridge 410, reducing the cost per assay results.

FIGS. 6 and 7 shows an alternative foil-based disposable cartridge 510 adapted for sample deposition including a cover layer 512, a middle layer 513, and a bottom layer 514 with spots 516 of binding sites. To this end, the cartridge comprises an inlet 515 with an enlarged opening. At this opening, a sample can be deposited, which is then transported by capillary forces through an internal channel to the sample chambers 517 of the middle layer 513.

In the cartridges 410 and 510, the form factor of the disposable cartridge is foil-based, which has the advantage that its volume can be very small (saving space in the instrument) and it can be made at low cost.

In a preferred embodiment, calibration information is provided for each lot of disposable cartridges such that liquid calibration steps are not needed. With each lot of disposable cartridges, calibration information could for example be provided in the form of an RF-ID, ROM-chip or barcode.

In summary, the proposed solution discloses a system architecture that is based on the use of disposable cartridges that have been pre-loaded with (dry) reagents. The main advantages of this concept are as follows:

instrument cost: fewer (expensive) robotics is required for all the reagent handling;

foot-print: fewer robotics enables making a smaller instrument taking up less expensive space in the laboratory;

dry-reagents: pre-loaded cartridge enable the use of dry reagents;

waste: when no liquid reagents are added less waste is created, reducing the cost for waste handling;

sensitivity: with dry reagents there is no dilution of the analyte improving sensitivity;

shelf life: dry reagents are more stable and can be stored for a longer period of time.

In the following, a particular cartridge design will be described with respect to FIGS. 8 to 14. The disclosed "open cartridges" can be used in any application that requires the use of a cartridge. In particular, they can be used in the systems described above, i.e. in a high throughput setting. It should be noted that the cartridges described in the following are usually assumed to comprise all reagents needed for at least one assay, though these are not always shown in the Figures. The cartridges are in general characterized in that they comprise
- a sample chamber that is accessible from the top;
- optical structures for incoupling and outcoupling of light with which a sample in the sample chamber can be examined (e.g. by FTIR).

An "open cartridge" 310 of this kind is schematically shown in FIGS. 8a-8c. It comprises a sample chamber 313 that is accessible from the top, as it is completely open to the top. On its bottom side, the cartridge 310 comprises two prismatic structures 316a, 316b through which light can be coupled in and out. The cartridge 310 can for example be produced as one piece by injection molding.

FIG. 8a shows particularly the addition of a sample with label particles comprised in a pipette-tip 301 to the cartridge. FIG. 8b shows the resulting thin layer of fluid in the open cartridge 310. FIG. 8c shows the positioning of magnets (only top magnet 302 is shown) to perform a magnetic assay. A possible contamination of the top coil 302 with the sample (although small amounts of liquid are not easily displaced) could be solved by closing the cartridge with a simple foil or cap after the liquid has been added.

The open cartridge provides the following advantages:
- There is no need to assemble a second part of the cartridge, resulting in a simpler, cheaper cartridge. The binding spots at the bottom of the sample chamber can simply be printed on the injection molded part and can be stored in a dry condition.
- There is also no need for small and complicated fluidic structures in the cartridge that are necessary for capillary filling, anti-bubble formation, fluidic stops etc., further simplifying the cartridge.
- As there is no need for separate fluid in- and outlets, the total area of the cartridge is decreased, making it more easy to perform multiple assays on a small area. The separate addition of particles and sample in two separate pipette steps is possible, which is not the case with a closed cartridge.

Figure 9:
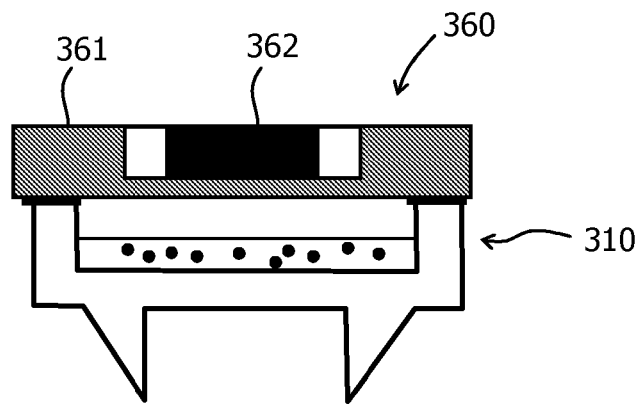
FIG. 9 schematically shows a cartridge with an open top side and a lid with an integrated magnet.

FIG. 9 shows how the cartridge 310 can be (reversibly) closed by a first cap or lid 360. The lid 360 consists of a carrier material 361 in which a magnet 362 is embedded. Instead of positioning a separate magnet above the open cartridge as shown in FIG. 8c, the lid 360 with the integrated magnet can be put upon the sample chamber. This has the advantage that the cartridge 310 is closed to prevent evaporation during the measurement. In this configuration, the lid 360 is part of the measurement device and is reused for each measurement. O-rings 363 (e.g. rubber) can optionally be used to effectively close the cartridge to prevent evaporation.

The closing of the cartridge as described above also offers the possibility of adding dry reagents (e.g. magnetic beads) to the lid. In this case the lid is typically a disposable. Because the dry reagents need to come in contact with the sample liquid, it is preferred that the entire sample chamber 313 is filled when applying the lid.

Figures 10, 11:
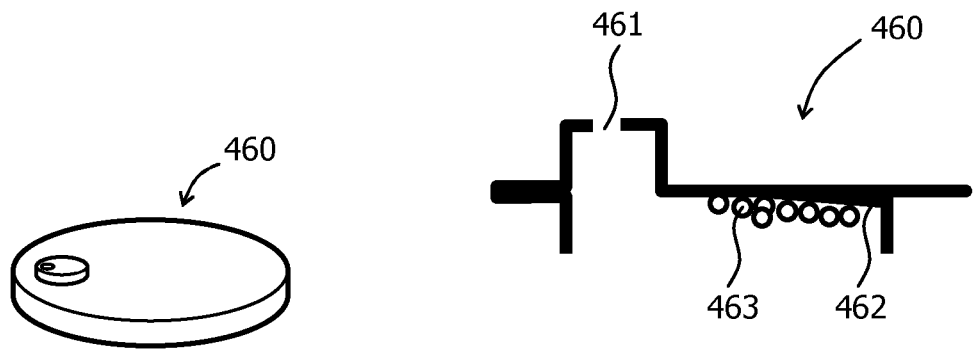
FIG. 10 shows a perspective view of a lid for a cartridge with an open top side.
FIG. 11 shows a section through the lid of FIG. 10.
Figure 12:
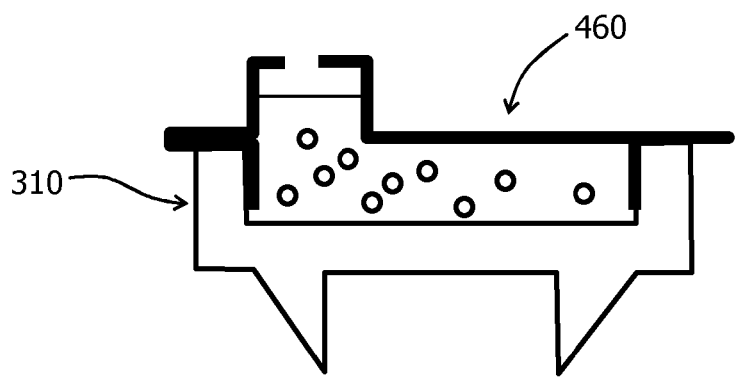
FIG. 12 shows the lid of FIG. 10 on a cartridge.

FIGS. 10 to 12 show a corresponding embodiment of a lid 460 with which the cartridge 310 can temporarily be closed. The lid 460 comprises dry reagents 463 on its interior surface 462. To prevent sample leaking out of the cartridge, an overflow chamber with air vent 461 is incorporated in the lid. To prevent air bubble enclosure, it is preferred that the interior surface 462 of the cap, facing the liquid, is slanted.

Figure 13:
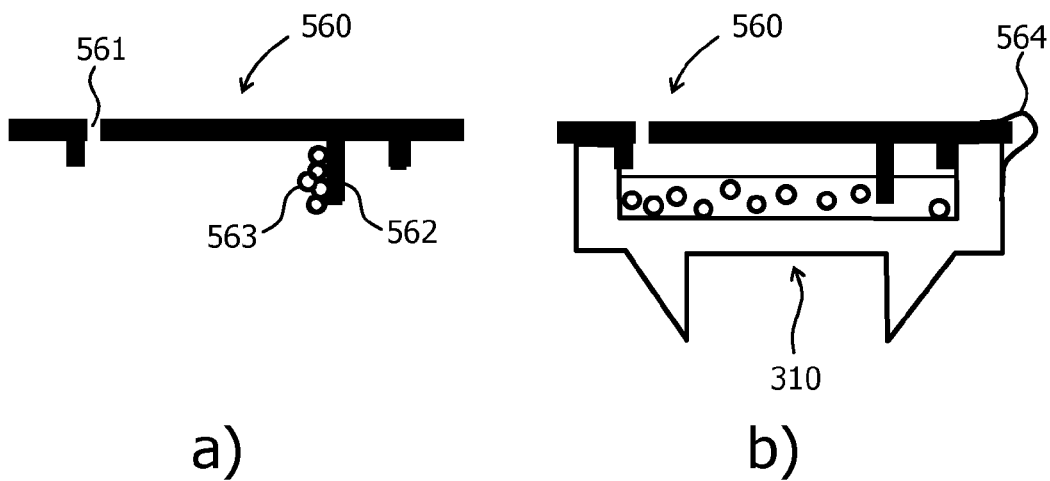
FIG. 13 schematically shows a cartridge with an open top side and a further embodiment of a lid.

FIG. 13 shows a different approach to bring reagents 563 in contact with the liquid in the sample chamber 313 without the need to fill the entire chamber. This is possible with a lid 560 comprising a protrusion 562 that extends into the liquid and onto which the reagents 563 are applied. An air vent 561 is provided to allow the escape of trapped gases. Moreover, the Figure indicates a hinge 564 (for example a film hinge) with which the lid 560 is attached to the cartridge 310.

Figure 14:
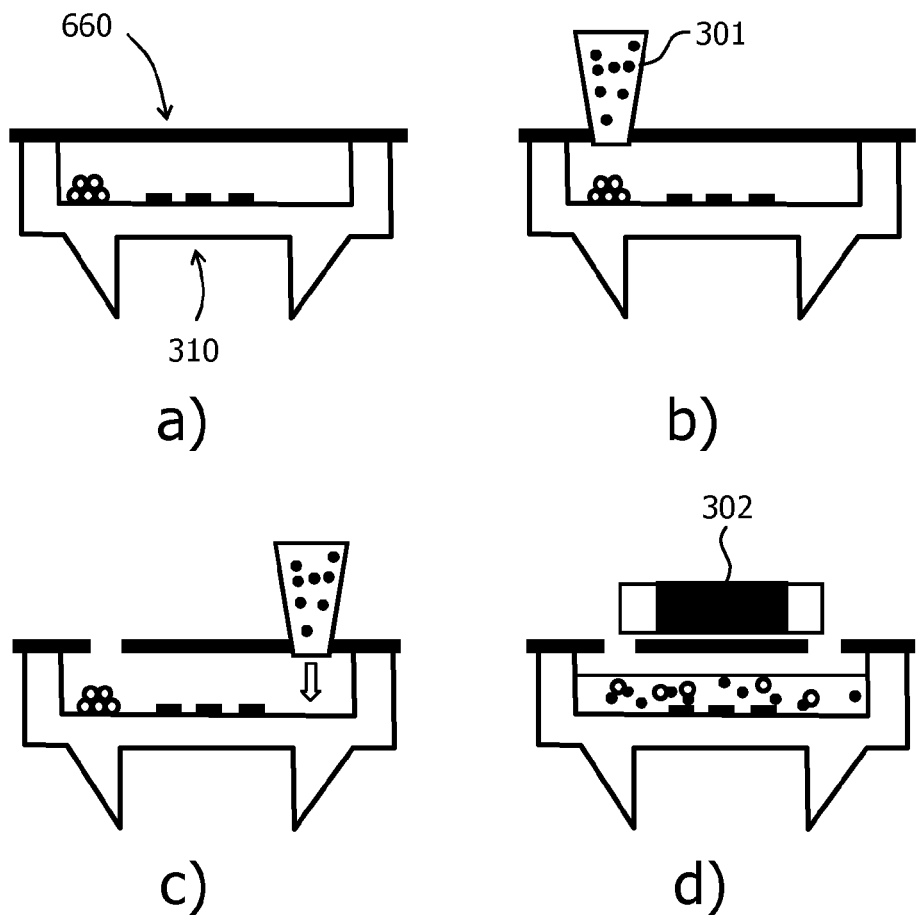
FIG. 14 schematically shows a cartridge with an open top side and a foil as a lid.

As shown in FIG. 14, the problem of contamination described above can be circumvented by closing the cartridge 310 with a foil 660 during manufacturing. Such a foil 660 has the additional advantage that it protects the sample chamber 313 from any external influences (dirt, moisture, physical contact etc.) during storage. The fluid can be added to the chamber 313 by pinching the foil 660 with a pipette-tip 301. To allow the enclosed air to flow out, the foil can be pierced with the pipette-tip twice, only releasing the fluid after the second time (cf. FIGS. 14b, 14c). FIG. 14d shows the positioning of magnets (only top magnet 302 is shown) to perform the magnetic assay.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A system for processing a sample according to a selected one of a plurality of assays, said system comprising:
   a plurality of cartridges in which processing of a sample can take place and where each cartridge contains a different set of reagents required for at least one of the assays, the reagents including magnetic particles as label particles that selectively bind to one target component;
   a manipulator for introducing a sample into a selected cartridge of the plurality of cartridges; and
   at least one actuation-device and an integrated actuation-and-readout device comprising a magnetic field generator,
   wherein the plurality of cartridges is configured to enable execution of a complete assay with a sample added to the cartridge without further liquid handling steps.

2. The system according to claim 1, wherein the system is accommodated in a housing.

3. The system according to claim 1, wherein the system can perform more than 20 tests/hour.

4. The system according to claim 1, wherein several copies of each cartridge are arranged in the reach of the manipulator.

5. The system according to claim 1, wherein at least one of several copies of each cartridge and a waste reservoir are arranged in the reach of the manipulator.

6. The system according to claim 1, further comprising at least one of:
   at least one readout-device in which target components of a sample can be detected,
   at least one actuation-device in which a sample comprised in a cartridge can be actuated, preferably by the action of electromagnetic fields and/or heat, and
   at least one integrated actuation-and-readout device.

7. The system or the method according to claim 6, wherein at least one of the at least one readout-device, the at least one actuation-device, and the at least one integrated actuation-and-readout device can be moved by the manipulator together with the cartridge.

8. The system according to claim 1, wherein at least one cartridge of the plurality of cartridges is provided with automatically readable information carriers.

9. The system according to claim 1, wherein at least one cartridge of the plurality of cartridges comprises a plurality of sample chambers in which different assays can be executed.

10. The system according to claim 1, wherein the plurality of cartridges has a sample chamber that is accessible from a top, and wherein the plurality of cartridges comprises optical structures for incoupling and outcoupling of light with which the sample in the sample chamber can be examined.

11. The system of claim 1, wherein the system can perform more than 50 tests/hour, most preferably more than 150 tests/hour.

12. The system of claim 1, wherein the system can perform more than 150 tests/hour.

13. A method for processing a sample in a system according to a selected one of a plurality of assays, said method comprising acts of:
  providing a plurality of cartridges in which the processing of a sample can take place and where each cartridge contains a different set of reagents required for at least one of the assays;
  introducing with a manipulator the sample into a selected cartridge of the plurality of cartridges,
  wherein the plurality of cartridges is configured to enable execution of a complete assay with the sample added to the cartridge without further liquid handling acts.

14. The method of claim 13, wherein the plurality of cartridges has a foil-based design.

15. The method of claim 13, wherein at least one of the plurality of cartridges comprises dry reagents.

16. The method of claim 13, wherein the reagents of the cartridge comprise at least one of binding sites that are specific for different target components, and label particles, that selectively bind to one target component.

17. A system for processing a sample according to a selected one of a plurality of assays, said system comprising:
  a plurality of cartridges in which processing of a sample can take place and where each cartridge contains a different set of reagents required for at least one of the assays, the reagents including magnetic particles as label particles that selectively bind to one target component;
  a manipulator for introducing a sample into a selected cartridge of the plurality of cartridges; and
  at least one actuation-device and an integrated actuation-and-readout device comprising a magnetic field generator,
  wherein the plurality of cartridges has a foil-based design.

18. A system for processing a sample according to a selected one of a plurality of assays, said system comprising:
  a plurality of cartridges in which processing of a sample can take place and where each cartridge contains a different set of reagents required for at least one of the assays, the reagents including magnetic particles as label particles that selectively bind to one target component;
  a manipulator for introducing a sample into a selected cartridge of the plurality of cartridges; and
  at least one actuation-device and an integrated actuation-and-readout device comprising a magnetic field generator,
  wherein at least one of the plurality of cartridges comprises dry reagents.

19. A system for processing a sample according to a selected one of a plurality of assays, said system comprising:
  a plurality of cartridges in which processing of a sample can take place and where each cartridge contains a different set of reagents required for at least one of the assays, the reagents including magnetic particles as label particles that selectively bind to one target component;
  a manipulator for introducing a sample into a selected cartridge of the plurality of cartridges; and
  at least one actuation-device and an integrated actuation-and-readout device comprising a magnetic field generator,
  wherein the reagents of the cartridge comprise at least one of binding sites that are specific for different target components, and label particles, that selectively bind to one target component.

* * * * *